(12) United States Patent
Wang et al.

(10) Patent No.: US 9,731,219 B2
(45) Date of Patent: Aug. 15, 2017

(54) METHODS AND DEVICES FOR OPEN-BED ATMOSPHERIC COLLECTION FOR SUPERCRITICAL FLUID CHROMATOGRAPHY

(75) Inventors: Ziqiang Wang, Lansdale, PA (US); Steven L. Zulli, Lincoln University, PA (US); Daniel Rolle, Bear, DE (US); Chuping Luo, Wilmington, DE (US); Harbaksh Sidhu, Allison Park, PA (US)

(73) Assignee: Waters Technologies Corporation, Milford, MA (US)

(*) Notice: Subject to any disclaimer, the term of this patent is extended or adjusted under 35 U.S.C. 154(b) by 206 days.

(21) Appl. No.: 14/125,957

(22) PCT Filed: Jun. 15, 2012

(86) PCT No.: PCT/US2012/042755
§ 371 (c)(1),
(2), (4) Date: Apr. 7, 2014

(87) PCT Pub. No.: WO2012/174437
PCT Pub. Date: Dec. 20, 2012

(65) Prior Publication Data
US 2014/0217031 A1    Aug. 7, 2014

Related U.S. Application Data

(60) Provisional application No. 61/498,458, filed on Jun. 17, 2011.

(51) Int. Cl.
*B01D 15/40* (2006.01)
*B01D 15/16* (2006.01)
(Continued)

(52) U.S. Cl.
CPC ........... *B01D 15/165* (2013.01); *B01D 15/24* (2013.01); *B01D 15/40* (2013.01); *G01N 30/80* (2013.01);
(Continued)

(58) Field of Classification Search
CPC ........ B01D 15/10; B01D 15/12; B01D 15/40; B01D 15/165; B01D 15/24; B01D 15/247;
(Continued)

(56) References Cited

U.S. PATENT DOCUMENTS 5,139,680 A    8/1992  Tarnopolsky
8,327,725 B2  12/2012  Kanomata
(Continued)

FOREIGN PATENT DOCUMENTS

WO    2006029330 A2    3/2006
WO    2010056313 A1    5/2010

OTHER PUBLICATIONS

Katalin Ebinger et al: Evaluation of a New Preparative Supercritical Fluid Chromatography System for Compound Library Purification: The TharSFC SFC-MS prep-100 System, Journal of Laboratory Automation, vol. 16, No. 3, Jun. 1, 2011, pp. 241-249.
(Continued)

*Primary Examiner* — Katherine Zalasky
(74) *Attorney, Agent, or Firm* — McCarter & English, LLP; Deborah M. Vernon (57) ABSTRACT

A supercritical fluid chromatography system comprises a first pump for pumping a first flow stream comprising a compressible fluid and a second pump for pumping a second flow stream comprising a modifier fluid. The second pump is in parallel with the first pump. A column is located in a combined flow stream. The column is located downstream of the first and second pumps. The combined flow stream
(Continued)

comprises the first flow stream, the second flow stream, and a sample. A detector is located downstream of the column. A gas-liquid separator is located downstream of the detector. The gas-liquid separator is configured to vent a majority of the compressible fluid while maintaining a majority of the sample, thus preventing aerosolization of the flow stream and minimizing sample loss as well as cross contamination. An open bed collector is located after the gas-liquid separator.

8 Claims, 9 Drawing Sheets

(51) Int. Cl.

| | |
|---|---|
| *B01D 15/24* | (2006.01) |
| *G01N 30/80* | (2006.01) |
| *G01N 30/62* | (2006.01) |
| *G01N 30/82* | (2006.01) |
| *G01N 30/02* | (2006.01) |

(52) U.S. Cl.
CPC ............ *B01D 15/247* (2013.01); *G01N 30/62* (2013.01); *G01N 30/82* (2013.01); *G01N 2030/027* (2013.01)

(58) Field of Classification Search
CPC ........ G01N 30/02; G01N 30/62; G01N 30/80; G01N 30/82; G01N 2030/027
See application file for complete search history.

(56) References Cited

U.S. PATENT DOCUMENTS

| | | | | |
|---|---|---|---|---|
| 8,591,734 | B2 | 11/2013 | Matabe | |
| 2001/0013494 | A1 | 8/2001 | Maiefski et al. | |
| 2002/0070169 | A1 | 6/2002 | Berger et al. | |
| 2002/0139752 | A1 | 10/2002 | Berger et al. | |
| 2004/0018099 | A1 | 1/2004 | Berger et al. | |
| 2006/0054544 | A1 * | 3/2006 | Roenneburg et al. | 210/198.2 |
| 2008/0010956 | A1 | 1/2008 | Fogelman et al. | |
| 2010/0163490 | A1 | 7/2010 | Lasalle | |

OTHER PUBLICATIONS

J Olson: Customization of a Commercially Available Prep Scale SFC System to Provide Enhanced Capabilities, Journal of the Association for Laboratory Automation, vol. 7, No. 4, Aug. 1, 2002, pp. 69-74.

* cited by examiner

METHODS AND DEVICES FOR OPEN-BED ATMOSPHERIC COLLECTION FOR SUPERCRITICAL FLUID CHROMATOGRAPHY

RELATED APPLICATIONS

This application is a U.S. National Stage application of International Application No. PCT/US2012/042755, filed on Jun. 15, 2012, which claims priority to U.S. Provisional Application No. 61/498,458, filed on Jun. 17, 2011, the entire contents of which are hereby incorporated by reference.

TECHNICAL FIELD

The present technology relates generally to methods and devices for open-bed atmospheric collection for supercritical fluid chromatography ("SFC"), and in particular to methods and devices for open-bed atmospheric collection with an XY type fraction collector (e.g., a collector arm with no Z-movement) for SFC.

BACKGROUND

Open bed type fraction collectors, for example, XY type fraction collectors, have been widely used in preparative liquid chromatography instruments for their flexibility, simplicity, efficiency, wide applicability, reliability and economy. The prior art collectors can include a platform that can accommodate various sizes of containers and configurations of rack adapters to hold tubes, bottles, vessels, pass-through/funnel-type connections as well as larger size containers for fraction collections. The collector can also have electrical components for automated control either through front panel or via direct control by sophisticated software communication protocols.

The actual collection of chromatography fractions is realized through liquid plumbing connections from chromatography instruments. After the fractions are separated from the column/cartridges in the chromatography system, they are transferred via connecting tubing to an XY type collector, flowing through a robotic arm collector tip, and are collected in containers underneath the robotic arm collector tip. The type of containers can be, for example, glass tubes, bottles, vessels, and/or pass-thru adapters, which can allow the fractions to be collected in larger size containers such as carboys. During the collection process, the robotic collector arm can move along the containers based on preset methodologies by the operator to realize the separation and collection of different fractions into their corresponding containers.

The XY type collector has wide applicability and can be used in various chromatographic systems, ranging from flash chromatography ("Flash"), low to mid-level pressure chromatography ("LPLC" and "MPLC," respectively) to high performance liquid chromatography ("HPLC"). The XY type collector can be controlled either manually, by using a preset method from the front panel or from programmed control via software for full automation of the chromatography system. XY type collectors, as their name implies, have adapter arms that can travel only in two dimensions, i.e. no Z-movement. Typically, the arm is disposed above a grid-formation of open collection vessels, for example test tubes in which the sample is collected. In the case of many chromatography setups such as "Flash," "LPLC," "MPLC," and "HPLC," there is no need for the adapter arm to move in the Z dimension because the eluent exiting the column can easily be directed to drip down into the open collection vessels under the action of gravity alone, i.e. the eluent is in liquid phase or liquid-solid phase. Thus the advantages of the XY type collector include but are not limited to ease of use, reliability, economy, and flexibility.

Supercritical Fluid Chromatography ("SFC") is a high-pressure, high performance chromatographic tool that can be used instead of liquid chromatography systems. Typically, today's SFC systems employ compressible fluids (e.g., carbon dioxide) at conditions above its supercritical point as a mobile phase, along with modifying solvents in most cases, to perform the chromatographic separation and purification processes. In general, SFC possesses higher efficiency, higher capacity and faster process times than other chromatography systems, for example, HPLC. SFC can significantly process more crude cleanup and separation/purification in less unit of measure, with significant reduction of toxic organic solvent waste by the use of carbon dioxide. It is therefore considered a green technique with high productivity and great economic impact.

SFC uses supercritical fluids such as carbon dioxide as the main flow solvents. The supercritical $CO_2$ is under controlled pressure while it is flowing in the SFC chromatography system. A pressure regulator, for example a back pressure regulator ("BPR") can be used to control the pressure of the $CO_2$ throughout the SFC system. The BPR is typically placed in the back end of the plumbing of the chromatography system. Once the fluids pass through the BPR and are transferred to collectors, the fluid is depressurized and supercritical $CO_2$ (as well as other compressible fluids) can be converted to gaseous vapor and vented. This leaves the sample fraction in minimal liquid volume to be collected. It is, therefore, a natural phenomenon that aerosols of liquids can be generated along with this depressurization process. The generated aerosols can carry the sample of interest from the separation process. Uncontrolled aerosols generated from this depressurization process can result in sample loss and cross contamination during collection after separation and detection, among other issues and risks, because the eluent does not simply drip straight down into a single open collection vessel, i.e. the eluent is at least partially aerosolized.

Due to the depressurization process that occurs when compressible fluids are used in an SFC system, existing collection designs for SFC chromatography use well-controlled collectors. For example, the location of the collection of the sample is enclosed inside a container that can control any resulting aerosol via means of pressure and dimensional measures. Therefore, the prior art designs typically put the location of the collection of sample inside a sealed vessel so that there is physically no chance for the aerosols to be released to the atmosphere under normal process conditions. The vessel can be made of, for example, stainless steel metal that can withstand the high pressures within an SFC process, or of glass/polymeric material with reduced pressure control (e.g., venting) at a reduced over-pressure risk level. The prior art designs can require dedicated designs with significant investment in hardware and software. This can prevent wider applicability and robustness of the collection system, among other impacts.

For several reasons, XY type collectors have not been used in SFC systems. For example, XY type collectors comprise a collector arm that is disposed above the containers, which means the location of the collection cannot be encapsulated into the sealed collection vessel. In addition, the collection arm does not have vertical movement (Z-movement, relative to X-Y plane/horizontal movement) to lower its tip down into the containers to confine the aerosols. This makes the integration of SFC instruments with XY type collectors problematic by their own design, even though there are numerous significant advantages for such integration (e.g., the combination of the high productivity of an SFC system with the flexibility, simplicity, efficiency, wide applicability, reliability and economy of an XY type collector).

SUMMARY OF THE TECHNOLOGY

The present technology is directed to a system and process for SFC that can incorporate a standard XY type collector (i.e. no Z movement) suitable for other types of chromatography such as HPLC, MPLC, LPLC and Flash chromatography. It is also directed to an SFC system that can be coupled to an open bed atmospheric XY type collector without the loss of sample and without cross contamination when the supercritical fluid reaches atmospheric conditions.

The technology enables the use of standard XY type fraction collectors in SFC. Such fraction collectors are known in the art for use with other chromatography systems, and may incorporate a robotic collector arm that can move along the containers based on preset methodologies by the operator to realize the separation and collection of different fractions into their corresponding containers. The technology also enables use of open-bed type collectors that do not require specialized collection vessels. For example, this technology obviates the need for sealed vessels made of stainless steel or some polymer or glass that can withstand high pressure.

In one aspect, the technology features a supercritical fluid chromatography system. The system comprises a first pump for pumping a first flow stream comprising a compressible fluid (e.g. $CO_2$) and a second pump for pumping a second flow stream comprising a modifier fluid (e.g. methanol). Typically, the modifier fluid is an incompressible fluid. The second pump is in parallel with the first pump. A column is located in a combined flow stream. The column is located downstream of the first and second pumps. The combined flow stream comprises the first flow stream, the second flow stream, and a sample. A detector is located downstream of the column. A gas-liquid separator is located downstream of the detector. The gas-liquid separator is configured to vent a majority of the compressible fluid while maintaining a majority of the sample to avoid sample loss and cross-contamination. An open bed XY type collector is located after the gas-liquid separator.

A compressible fluid is one in which the fluid density changes significantly when it is subjected to high pressure. The key difference, in the context of SFC, between compressible and incompressible fluids is the way the different fluids behave when pressure is applied to them. In the case of incompressible fluids, e.g. water or methanol, application of a pressure at one point immediately creates identical pressure at all other points in the system.

In the case of a compressible fluid, e.g. supercritical $CO_2$, the imposition of a force at one point within a system does not result in an immediate increase in pressure elsewhere the system. Instead, the fluid compresses near where the force was applied; that is, its density increases locally in response to the force. This compressed fluid subsequently expands against neighboring fluid particles causing the neighboring fluid itself to compress. In many cases, the net result is the generation of pressure waves as the locally dense fluid moves throughout the system.

In one or more embodiments of the above aspect, sample loss and cross contamination are reduced by the incorporation of one or more devices that limit aerosolization, for example the GLS. In one or more embodiments, the supercritical fluid chromatography system can also include a collector arm located downstream of the gas-liquid separator. In some embodiments, the supercritical fluid chromatography system includes a collector arm adapter coupled to the collector arm. The collector arm adapter can be configured to further reduce aerosols when the combined flow stream is at atmospheric conditions. In some embodiments the container rack is adjustable.

In some embodiments, the gas-liquid separator is made from stainless steel, an appropriate polymer, or glass. In some embodiments, a back pressure regulator can be located upstream of the gas-liquid separator. In some embodiments, the compressible fluid is carbon dioxide ($CO_2$).

The current technology also features a method for collecting multiple samples in supercritical fluid chromatography (SFC). The method includes pumping a first flow stream comprising a compressible fluid and pumping a second flow stream comprising an incompressible fluid. The method further includes injecting a sample into the second flow stream and combining the first and second flow streams to form a combined flow stream, then subjecting the flow stream to SFC conditions. The method further includes flowing the combined flow stream through a chromatography column and removing at least a portion of the compressible fluid from the combined flow stream followed by collecting the sample in an open bed XY type collector.

In some embodiments, the compressible fluid used in the method is $CO_2$. In some embodiments, aerosolization of the sample is prevented during collection of the sample in the open-bed XY collector.

The exemplary methods and devices of the present disclosure provide numerous advantages. For example, this technology significantly improves and expands the scope of SFC technology for use in a variety of settings, including the chemical industry and academic research laboratories. By eliminating technical concerns such as cross contamination, sample loss, and unsafe venting of compressed fluids, the technology makes SFC a more robust and reliable process. Additionally, the technology makes SFC a more convenient process because it allows the use of standard, open bed atmospheric XY type fraction collectors already in use with other types of chromatography and familiar to one of ordinary skill in the art.

BRIEF DESCRIPTION OF THE DRAWINGS

The foregoing and other features and advantages provided by the present disclosure may be better understood by referring to the following description taken in conjunction with the accompanying drawings. The drawings are not necessarily to scale, emphasis instead generally being placed upon illustrating the principles of the technology.

DETAILED DESCRIPTION

In order to prevent sample loss and cross-contamination when collecting fractions for SFC, the technology takes advantage of a gas-liquid separator (GLS) installed into a flow stream after a BPR, of which the purpose is to vent the majority of gaseous carbon dioxide ($CO_2$), or any supercritical fluids used in the process, while maintaining the incompressible modifying liquid in which the sample is dissolved. Although $CO_2$ may be one common supercritical fluid used for SFC, other suitable supercritical fluids may be nitrous oxide ($N_2O$), sulfur hexafluoride ($SF_6$), or chlorofluorocarbons (CFCs) such as Freon. One of ordinary skill in the art can vary the dimensions, geometry and the operational settings of the GLS to optimize the GLS so that it is suitable for flow rates ranging from approximately a few mil/min to hundreds of ml/min.

The GLS, described in International publication number WO 2010/056313, hereby incorporated by reference in its entirety, comprises a chamber in which a specially tapered tube with an increasing internal diameter is inserted. The end of the tapered tube is angled such that as the gas-liquid mixture flows out of the tapered tube and into the larger chamber, flow is directed to impact an inner wall of the chamber at an angle tangential to the impact wall of the separator.

Because the gas-liquid flow is not straight down upon exiting the tapered tube, coalescence of the modifying liquid and sample begins inside the GLS. The impact point and angle of impact serve to direct the liquid stream into a downward spiral towards a liquid exit point. Simultaneously, compressible fluids such as $CO_2$ are vented upon exiting the tapered tube. Because the modifying liquid and sample coalesce in a controlled manner inside the GLS as the compressible fluid is vented, the modifying liquid and sample are able to drain towards the bottom of the GLS.

In embodiments, after passing through the GLS, the modifying liquid has been separated from the compressible fluid such as $CO_2$ and therefore is no longer in danger of being aerosolized. The modifying liquid now behaves just as any other mobile phase fluid common to other types of chromatography such as HPLC, MPLC, LPLC or Flash chromatography. Therefore, it can be collected using a standard open bed XY type fraction collector known to one of skill in the art without fear of sample loss or cross contamination.

Some embodiments of the technology further comprise a collector arm adapter (see e.g., FIG. 3A) that can be attached to an XY type collector arm that can be downstream of the GLS. The function of this collector arm adapter is to curb and/or diminish the aerosols generated once the fluid flow is subject to atmospheric conditions, for example, the location where the fluid flow leaves the collector tip of the robot arm. For example, the collector arm adapter is appropriate in the event that trace residual amounts of $CO_2$ (e.g. 0.001%-1%, 0.01%-0.1%) remain in the flow stream after passing through the GLS. The collector arm adapter includes a cover that surrounds a tip which disperses the sample to the collector rack. The collector arm adapter creates an enclosure to trap any remaining aerosols that may be generated as a result of trace residual $CO_2$ left in the incompressible fluid after the combined stream has passed through the GLS. By coupling the GLS to the collector arm adapter, the aerosols can be well confined within a very limited range around the fluid flow stream between the space where the stream leaves the collector and the container underneath the collector, at a significantly reduced scale. In some embodiments, the aerosols are completely diminished and are not observable in this design.

The process can include an adjustable container rack that can be coupled to the GLS and collector arm adapter. Corresponding dimensions and openings of receiving ports of the container rack, in addition to the adjustable height of the rack, can accommodate a wide range of fluid flow characteristics to ensure high collection efficiency of fraction flow.

Figure 4:
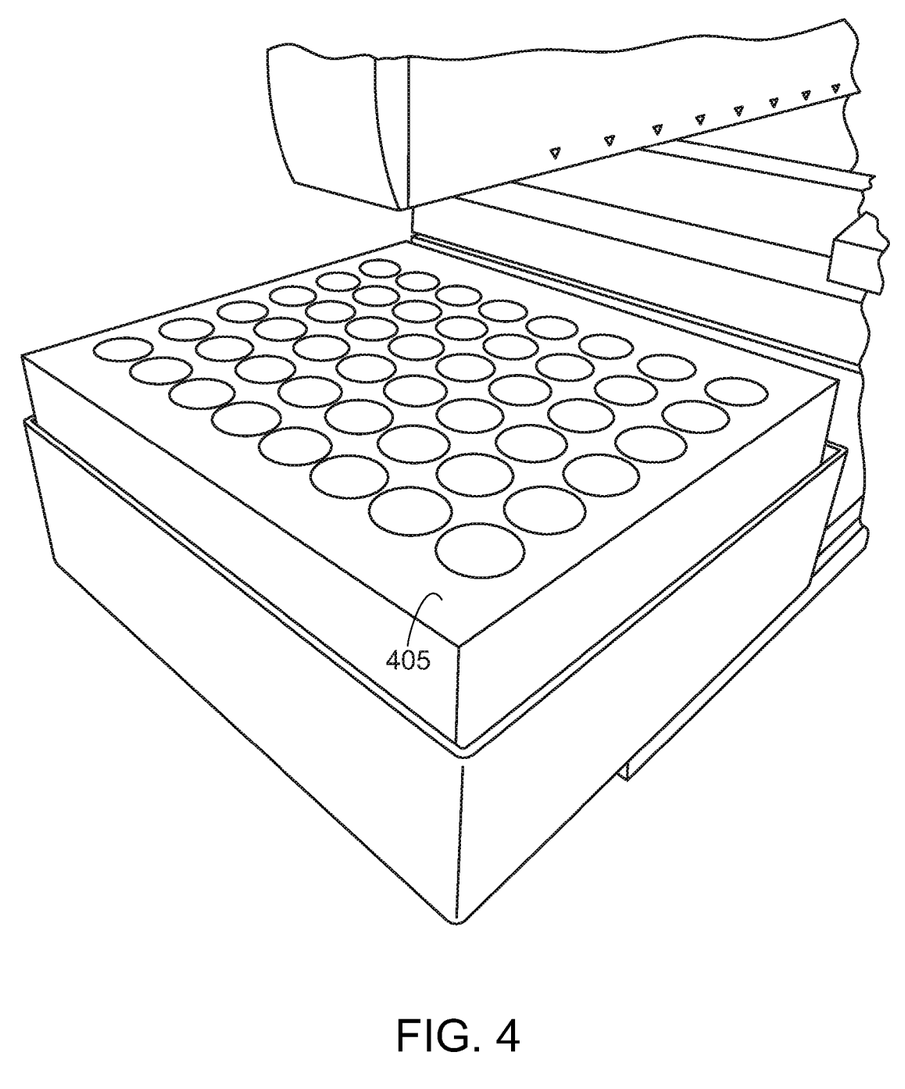
FIG. 4 shows one embodiment of a rack adapter design on WFCIII that is compatible with SFC instrumentation, according to an illustrative embodiment of the technology.
Figure 5:
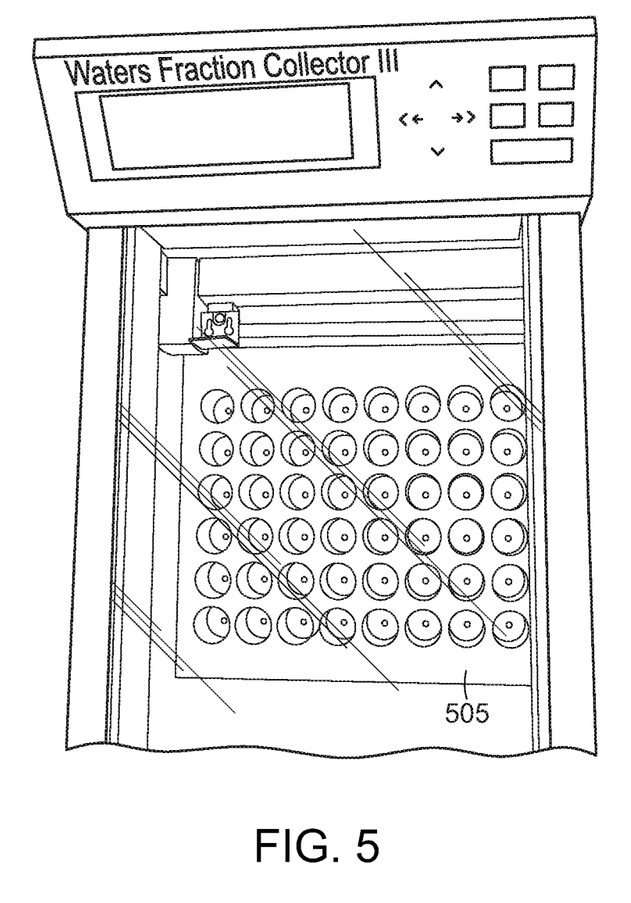
FIG. 5 is a top view of a rack adapter design on WFCIII that is compatible with SFC instrumentation, according to an illustrative embodiment of the technology.

The technology can also include optimum processes for hardware development for characteristic SFC instrumentation. The processes can include designs of GLS and collector arm adapters based on actual SFC flow characteristics to optimize the capability for maximum control of gas venting and aerosol diminishing. The GLS can be made of stainless steel, a polymer, glass or other types of compatible materials for the process. The geometry and dimensions of the GLS can be commensurate with the actual flow capacity to ensure proper ventilation flow while preserving most fluid flow drained down to the collector. The collector arm adapter (see, e.g., FIGS. 3A and 3B) can include various dimensions and geometries for optimized aerosol confinement and diminished capability based on flow rate and compositions. The rack adapter (see, e.g., FIGS. 4 and 5) can include designs for adjustable height and for accommodation and connection to various types of containers from, for example, tubes, bottles, and vessels, to carboys, to ensure maximum collection efficiency, encapsulation of liquid flow and minimum aerosol generation.

The present technology can also include optimum processes for method development. The processes can include optimization of method parameters such as pressure settings on GLS, which can range from about a few psi to 50-60 bar, combined with specific adapted geometry and dimensions for the best performance for gas-liquid separation and venting. The process can also include adjustment of the collector arm adapter in terms of its dimensions and spatial arrangement on the robot arm for best efficiency of aerosols control.

The present technology also includes various integrations of applications for the methods and devices for fraction collection purposes. Such development with an XY type collector includes, but is not limited to, routine fraction collections from high performance SFC, secondary collection in addition to conventional fraction collection in SFC, fraction collection for high flow, high speed supercritical fluid flash chromatography, and any other type of pressurized liquid processes where there is potential risk of aerosol generation during the collections.

Figure 1:
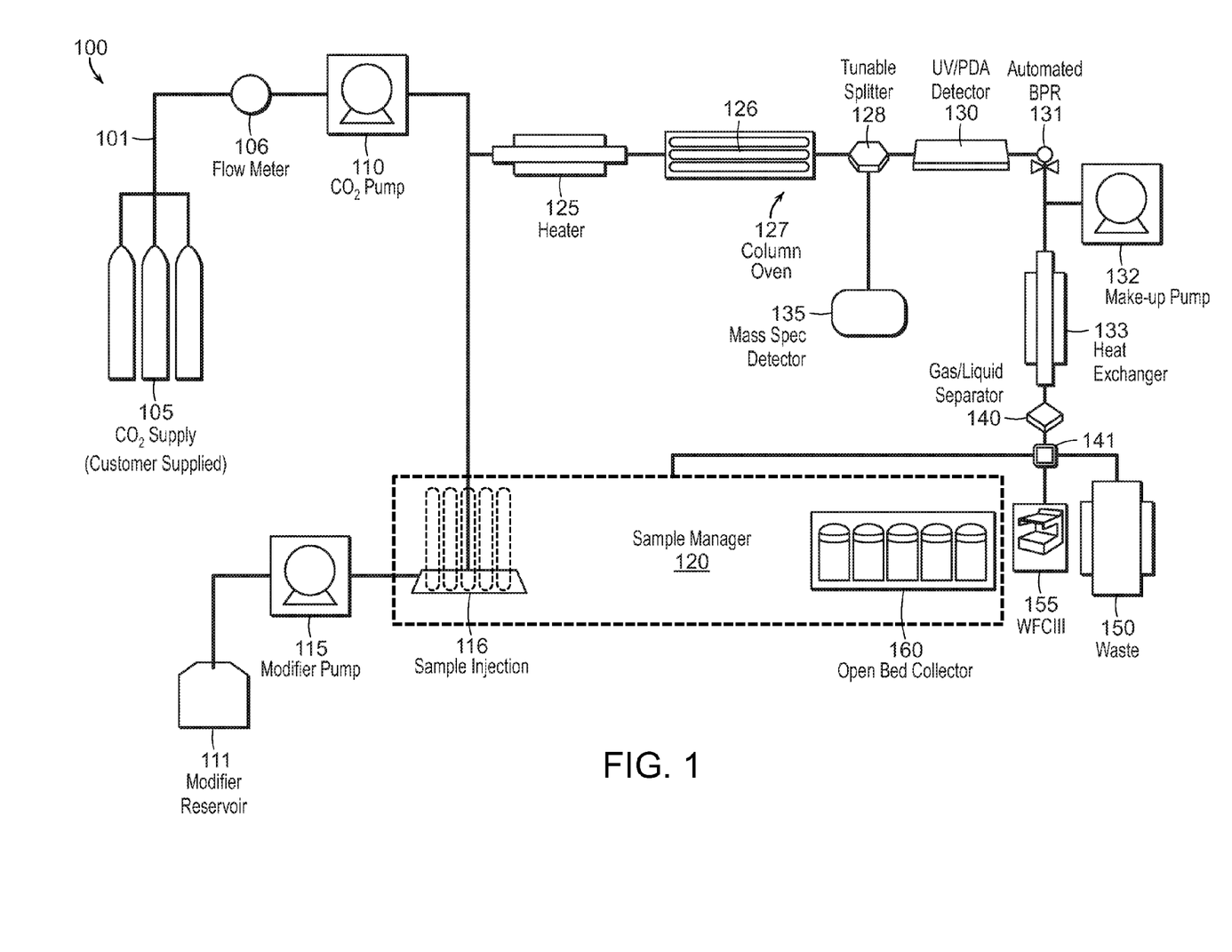
FIG. 1 is a diagram of an SFC system with an open-bed XY type collector, according to an illustrative embodiment of the technology.

One such embodiment of the above mentioned technology is depicted in FIG. 1, which shows a mass-directed preparative SFC100 (MD-SFC100) system 100. The components of the system are interconnected via a suitable tubing 101 that is capable of withstanding the intense pressures and temperatures necessary to reach supercritical conditions without corrosion or other safety concerns. In one embodiment, the system comprises a $CO_2$ supply 105, followed by a flow meter 106 to control the flow of $CO_2$ through the system. There is also a separate reservoir 111 which contains the modifier solvent, e.g. methanol. In some embodiments, there are pumps for both $CO_2$ and modifier solvents 110, 115, respectively. In some embodiments, there is a Waters 2767 sample manager 120 (including a sample injection 116 and an open bed collector 160). There are also in-line heaters 125, a separation column 126 surrounded by a column oven 127. In some embodiments, there is a tunable splitter 128 that directs a portion of the flow to a mass spectrometry detector 135 and a remaining portion of the flow to a UV/PDA detector 130. In some embodiments, there is an automated BPR 131 located downstream of the UV/PDA detector. There is a make-up pump 132 located downstream of the BPR, and a heat exchanger 133. In some embodiments, the GLS 140 is used to remove the compressible fluid (e.g. 100% removal, 99.98% removal, 99.8% removal, 99% removal) from the combined flow stream and vent it without aerosolization and corresponding sample loss and cross contamination. After a junction point 141 a portion of the stream is directed to a waste receptacle 150 while the remaining flow is directed to a fraction collector 160 shown here as a Waters 2767 fraction collector and a Waters Fraction Collector (WFCIII) 155. In this configuration the Waters Fraction Collector (WFCIII), an XY type fraction collector, is integrated as the secondary collector. WFCIII is plumbed along side with Waters 2767 fraction collector 160, and is controlled by Waters Masslynx software that controls the whole chromatography system 100. In one embodiment, the Waters 2767 fraction collector 160 is the primary fraction collector and is responsible for collecting the majority of fractions. In one embodiment, the WFCIII can optionally be used as a secondary fraction collector 155. The purpose of the optional secondary collector 155 is to collect any fractions that may be missed by the primary collector 160. For example, glitches in software or other unforeseen circumstances may prevent the primary collector from collecting all fractions, thus the secondary collector may be present to collect any uncollected fractions. Thus in some embodiments it is possible to use only one fraction collector (e.g. Waters 2767 fraction collector 160) whereas in some embodiments it is possible to use multiple fraction collectors.

In other embodiments, not shown, the system 100 can be used in combination with other fluids for performing SFC. That is, other compressible fluids which can be processed to form a supercritical phase for chromatography can be used in place of $CO_2$. For example, in one embodiment, nitrous oxide ($N_2O$) may be used. Alternatively, in one embodiment, other compressible fluids such as sulfur hexafluoride ($SF_6$) or chlorofluorocarbons (CFCs) such as Freon may be used.

Figure 2:
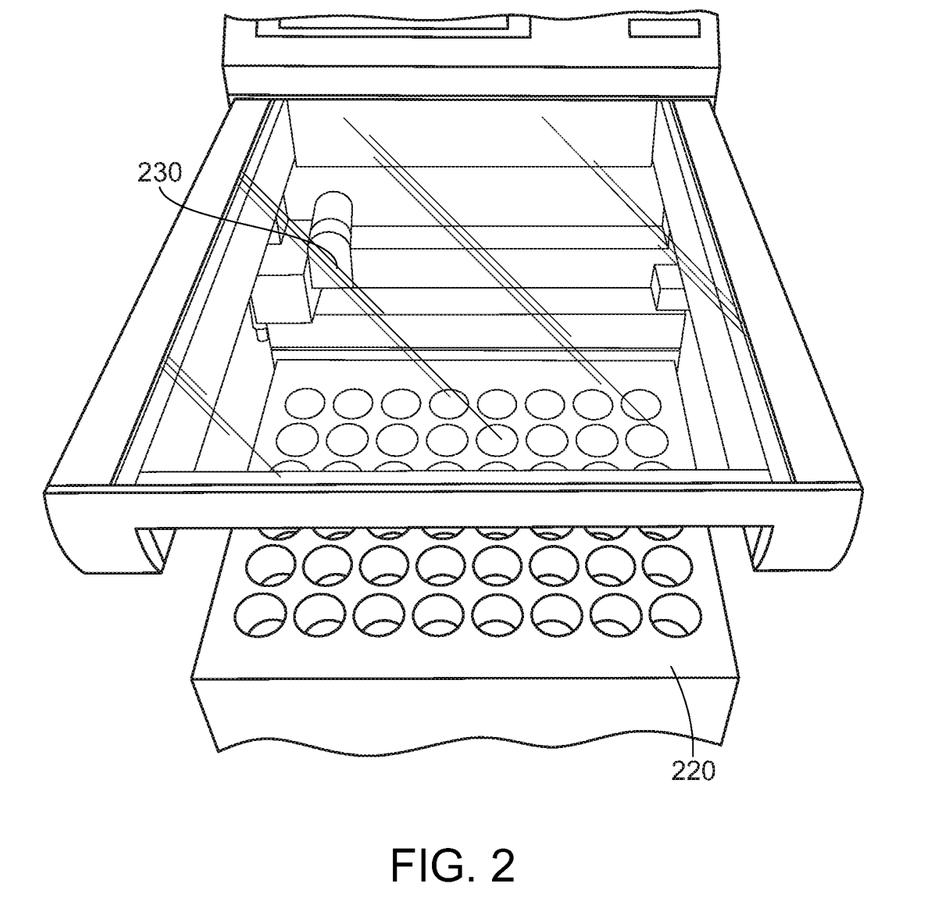
FIG. 2 shows the installations of Waters Fraction Collector III ("WFCIII"), an XY type collector installed with both a collector arm adapter and a rack adapter for SFC instrumentation, according to an illustrative embodiment of the technology.

FIG. 2 shows the installation of WFCIII, (e.g. part number 155 in FIG. 1) an XY type collector installed with both collector arm adapter 230 (for example, the collector arm adapter 305 of FIG. 3A) and rack adapter 220 (for example, the rack adapter 405 in FIGS. 4 and 505 in FIG. 5) for SFC instrumentation. In this embodiment, the collectors work to collect fractions of compounds of interest based on criteria set by instrument methods from UV, Mass Spectrometer and/or Evaporative Light Scattering Detector ("ELSD") and other signals. The WFCIII collector can be fully integrated and controlled by operating software that controls the entire chromatography system. The WFCIII works with the Waters 2767 collector in either a complementary way to ensure higher collection efficiency, or the Waters 2767 collector acts as a standalone collector. WFCIII can be trigged by line of injection, peak-based signals from Mass Spec., UV, ELSD or any kind of detectors from the system, and different kinds of algorithm combinations with these signals, or it can collect fractions by time windows, peak-triggered time slicing mode, or any other manual mode controllable by preset methodologies. The configuration in this embodiment can ensure a high collection efficiency and can reduce the risk of potential sample loss from random malfunction. The configuration can also enrich versatile collection features to further extend the applicability, robustness, economy and flexibility of SFC instrumentation for more chromatography applications, such as, but not limited to, high throughput analysis and purifications, chiral analysis, flash chromatography for pharmaceutical, natural product, food analysis, environmental monitoring, petroleum analysis, and/or alternative energy development.

Figure 3A:
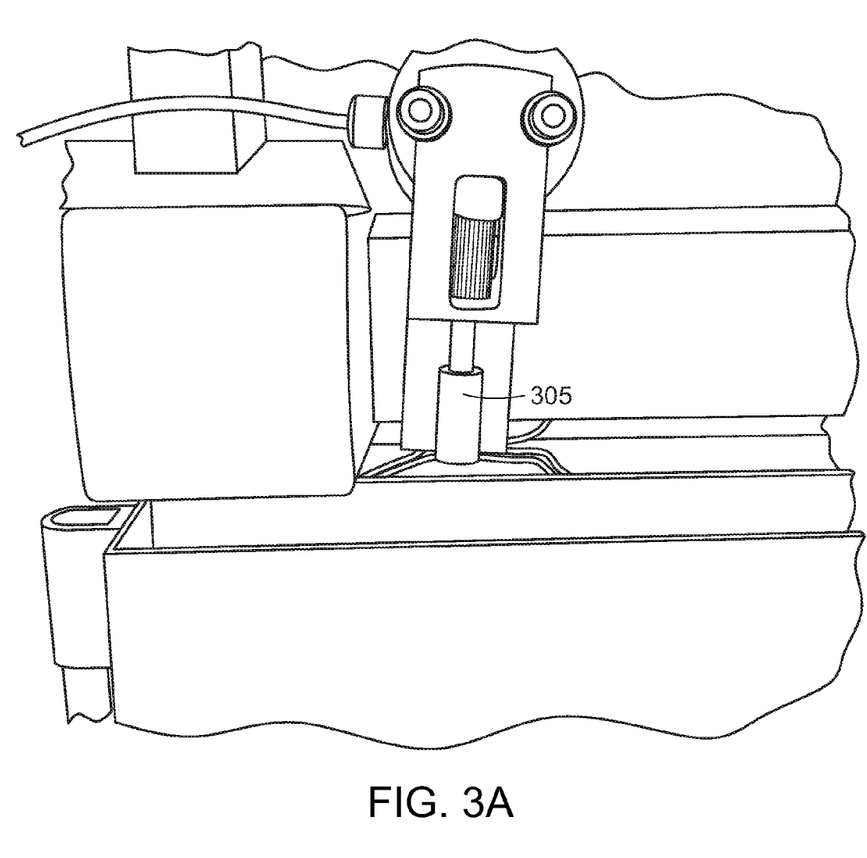
FIG. 3A shows the collector arm adapter design on a WFCIII, according to an illustrative embodiment of the technology.

The collector arm adapter 305 of FIG. 3A is an optional feature. In the event that not all of the $CO_2$ or compressible fluid is vented and some small portion remains, the adapter arm 305 can prevent sample loss/cross contamination by confining the space around the exit tip.

Figure 3B:
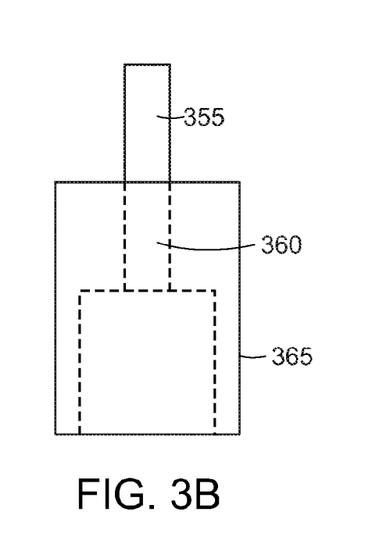
FIG. 3B shows a schematic representation of the collector arm adapter, according to an illustrative embodiment of the technology.

FIG. 3B shows a schematic of the internal geometry of the collector arm adapter pictured in 3A, i.e. adapter 305. Fluid enters through the inlet 355, and flows through outlet 360. Any aerosolization resulting from this transition is collected by the enclosure portion 365. In one embodiment, the inlet portion 355 is 8 mm in length. In one embodiment, the outlet portion 360 is 6 mm in length. In one embodiment, the enclosure element 365 is 14 mm in length.

While the collector arm adapter 305 is an optional element, which can enhance performance, the GLS is a required component. The GLS vents a significant portion (e.g. 100%, 99%) of the $CO_2$ from the combined flow stream.

Figure 6:
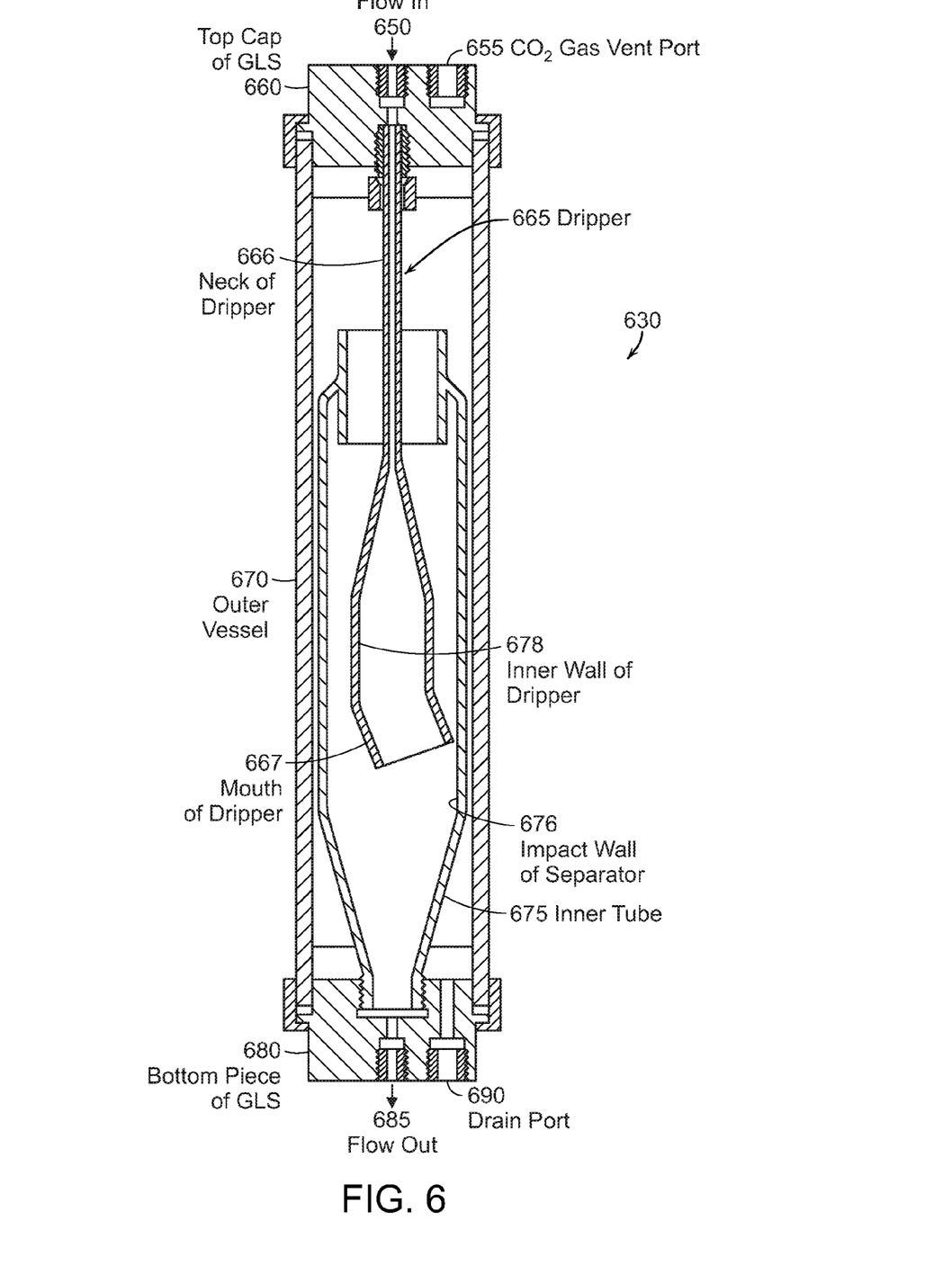
FIG. 6 is a diagram of an embodiment of the gas-liquid separator used in the technology.
Figure 7A:
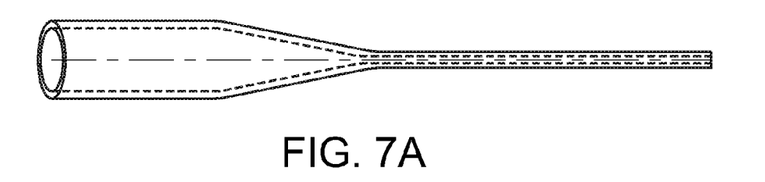
FIG. 7 shows diagrams of an embodiment of a dripper of the gas-liquid separator used in the technology.
Figure 7B:
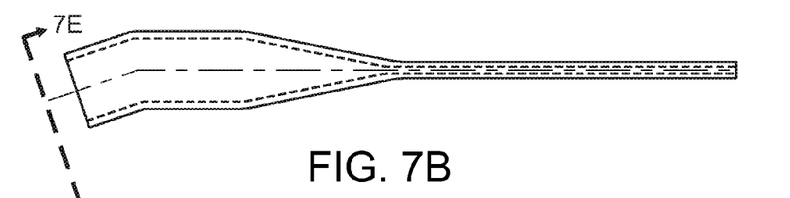
Figure 7C:
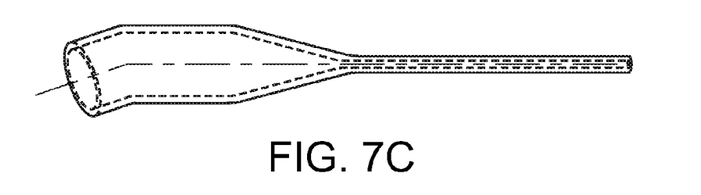
Figure 7D:
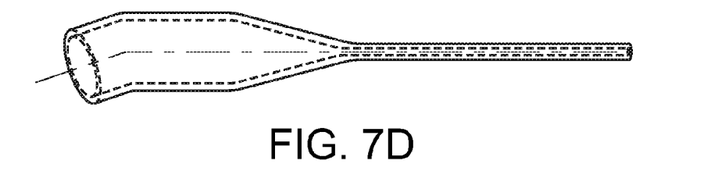
Figure 7E:
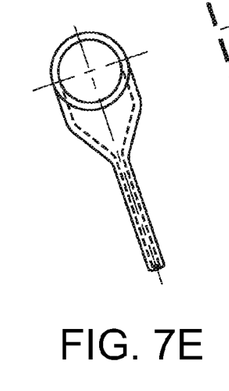

The gas-liquid separator used in the system of FIG. 1, e.g. GLS 140, is shown in more detail in FIG. 6. The separator comprises an inlet flow port 650, a gas vent 655, a top cap 660, an outer vessel 670, a bottom cap 680, a liquid outflow port 685, and a drain port 690. A specially tapered tube with an increasing internal diameter, called the dripper 665, is inserted into the separator. The mouth of the dripper 667 (through which the flow exits the dripper into the separator, the outlet) is wider than the diameter of the dripper where the flow enters the dripper 666 (inlet). The dimensions of the dripper are optimized for the system's flow rates, which assist in consolidating aerosol into a unified liquid stream. In general, the ratio of the diameter of the outlet to the diameter of the inlet is between 2-100 to one. For flow rates up to about 100 gm/minute, the ratio of the diameter of the outlet to the diameter of the inlet is between about 2-4 to one, preferably about three to one. The ratio can be adjusted to accommodate flow rates of up to 1000 gm/minute.

The dripper shown in FIG. 7, e.g. the dripper 665 of FIG. 6, has an angle, relative to the separator's downward pointing vertical axis, between 10 and 80 degrees. In other words, the exit of the dripper is neither straight down nor straight sideways, but rather in-between. This angle is in a vertical orientation, and is not the tangential angle.

Figure 8:
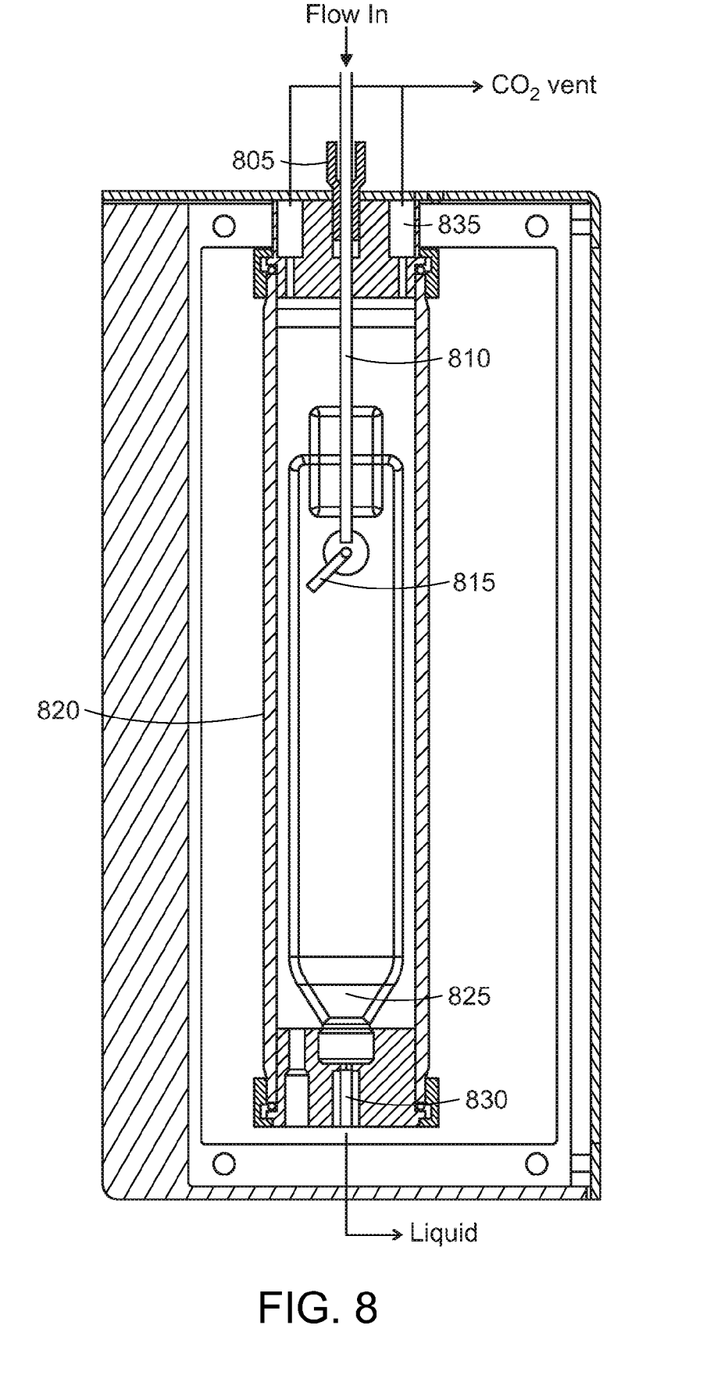
FIG. 8 shows another embodiment of the gas-liquid separator used in the technology.

Another embodiment of the GLS is shown in FIG. 8. Flow is directed into the GLS via the inlet port 805. As the fluid travels through the dripper 810, it exits through the mouth of the dripper 815. The incompressible fluid collects on the inner wall 820 and falls under the action of gravity towards the collecting basin 825 and finally flows through the outlet 830. Meanwhile, the compressible fluid escapes through the gas vent 835.

The GLS can be located anywhere downstream of the BPR and, most effectively, upstream of the fraction collectors. In one embodiment shown in FIG. 1, the GLS is located after the heat exchanger. In another embodiment, a plurality of gas-liquid separators may be located after the junction point 141.

Figure 9:
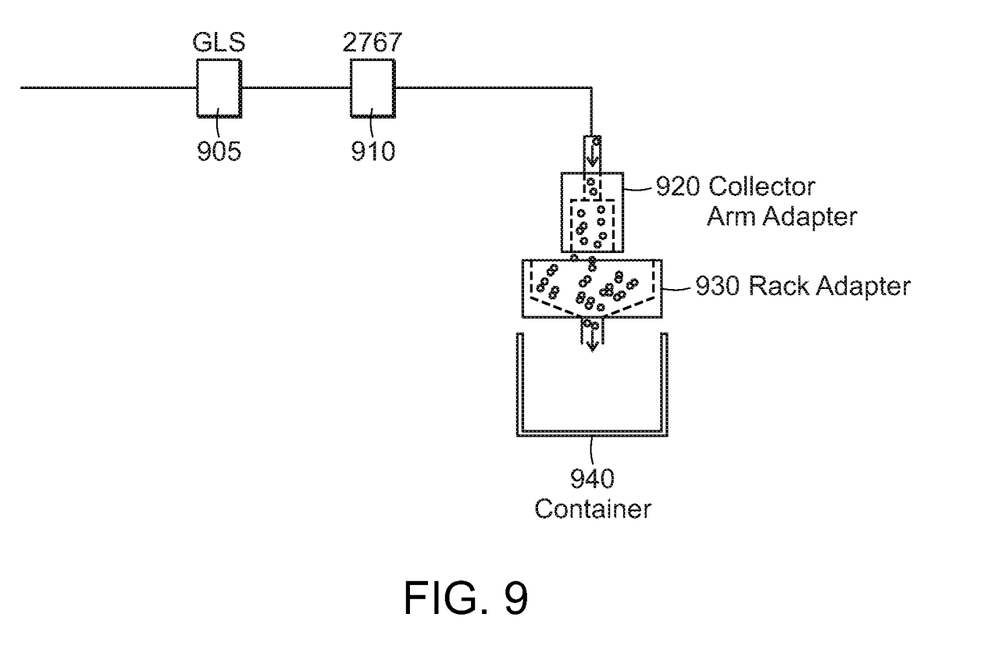
FIG. 9 shows a schematic embodiment of the open bed atmospheric collection system.

FIG. 9 shows a schematic embodiment of the open bed atmospheric collection system. It shows the collector arm adapter working in combination with the rack adapter to deliver the sample to the container. Fluid flows in through the GLS 905 (i.e. the GLS 140 in FIG. 1). After a portion of the sample is collected by the primary fraction collector 910, i.e. the Waters 2767 fraction collector 160 from FIG. 1, a portion of the sample passes through the collector arm adapter 920, i.e. part 305 shown in FIG. 3A. Any remaining traces of aerosols are collected by the rack adapter 930, i.e. part 220 in FIG. 2, part 405 in FIG. 4, and part 505 in FIG. 5. The fractions then pass into the container 940.

The technology described above can adapt to XY type fraction collectors with no Z-movement (e.g., movement in a vertical direction) arm for preparative SFC use. The technology can modify existing XY type fraction collectors with no Z-movement so that the collector meets the requirements of both technical and safety usage in SFC systems. Safety concerns can arise when aerosols are generated outside of the SFC system. Additionally, by reducing the presence of aerosols, the technology significantly reduces sample loss and cross contamination when collecting fractions.

This technology significantly improves and expands the scope of SFC technology for use in a variety of settings, including the chemical industry and academic research laboratories. By eliminating technical concerns such as cross contamination, sample loss, and unsafe venting of compressed fluids, the technology makes SFC a more robust and reliable process. Additionally, the technology makes SFC a more convenient process because it allows the use of standard, open bed atmospheric XY type fraction collectors already in use with other types of chromatography and familiar to one of ordinary skill in the art.

The technology can be used in any process where there is a danger of unwanted aerosols being generated. The flow conditions of the system can be optimized to diminish aerosols generated from depressurization of pressurized fluids to ensure collection efficiency and safety operation under atmospheric conditions.

Although various aspects of the disclosed apparatus and method have been shown and described, modifications may occur to those skilled in the art upon reading the specification. The present application includes such modifications.

What is claimed is:

1. A supercritical fluid chromatography system comprising:
    a first pump for pumping a first flow stream comprising a compressible fluid;
    a second pump for pumping a second flow stream comprising a modifier fluid, the second pump in parallel with the first pump;
    a column located in a combined flow stream, the column located downstream of the first and second pumps, the combined flow stream comprising the first flow stream, the second flow stream, and a sample;
    a detector located downstream of the column;
    a gas-liquid separator located downstream of the detector, the gas-liquid separator configured to receive and separate the combined flow stream into a compressible fluid flow and a remaining flow, the gas-liquid separator further configured to vent a majority of the compressible fluid while maintaining a majority of the sample to avoid sample loss and cross-contamination resulting in the remaining flow;
    a collector arm located downstream of the gas-liquid separator positioned to receive the remaining flow;
    a collector arm adapter coupled to the collector arm, the collector arm adapter configured to reduce aerosols when the remaining flow is at atmospheric conditions; and
    an open bed XY type collector located downstream of the collector arm adapter and positioned such that the remaining flow is directed to pass through the collector arm and into the open bed XY type collector.

2. The supercritical fluid chromatography system of claim 1, further comprising an adjustable container rack coupled to the open bed XY type collector.

3. The supercritical fluid chromatography system of claim 1 wherein the gas-liquid separator is made from stainless steel, polymer, or glass.

4. The supercritical fluid chromatography system of claim 1 further comprising a back pressure regulator located upstream of the gas-liquid separator.

5. The supercritical fluid chromatography system of claim 1 wherein the compressible fluid is carbon dioxide ($CO_2$).

6. The supercritical fluid chromatography system of claim 1, wherein the collector arm adapter comprises an inlet, an outlet, and an enclosure portion, the inlet positioned to receive the remaining flow and conduct the remaining flow to the outlet, the outlet positioned to release the remaining flow into a space around the outlet, and the enclosure portion positioned to confine the space around the outlet.

7. The supercritical chromatography system of claim 6, wherein the enclosure portion is sufficiently large that substantially all aerosols resulting from the release of the remaining flow into the space around the outlet are collected by the enclosure portion.

8. The supercritical fluid chromatography system of claim 6 wherein the enclosure portion is concentric with and wider than the outlet.

* * * * *